US00PP30917P2

(12) United States Plant Patent
Clark et al.

(10) Patent No.: US PP30,917 P2
(45) Date of Patent: Oct. 1, 2019

(54) BASIL PLANT NAMED 'UF16-23-2'

(50) Latin Name: ***Ocimum* x *hybrida***
Varietal Denomination: UF16-23-2

(71) Applicant: Florida Foundation Seed Producers, Inc., Marianna, FL (US)

(72) Inventors: David G. Clark, Gainesville, FL (US); Adam Moseley, Gilmanton Iron Works, NH (US); Shannon Bly, Fort Pierce, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/932,769

(22) Filed: Apr. 23, 2018

(51) Int. Cl.
*A01H 5/12* (2018.01)
*A01H 6/50* (2018.01)

(52) U.S. Cl.
USPC ..... Plt./258

(58) Field of Classification Search
USPC ..... Plt./258
CPC ..... A01H 5/12; A01H 5/02; A01H 6/50
See application file for complete search history.

(56) References Cited

PUBLICATIONS

Floriday Foundation Seed Producers, Inc. ITN 18-14—Amazel 'UF16-23-2' Basil Cultivar, retrieved on Mar. 28, 2019, retrieved from the Internet at http://www.ffsp.net/wp-content/uploads/2018/04/ITN18-14-final.pdf, 8 pp. (Year: 2018).*
Nassar et al. Botanical Studies on *Ocimum basilicum* L. (Lamiaceae) Research Journal of Acriculture and Biological Sciences, 9(5): 150-163, 2013. (Year: 2013).*
Raker Basil Amazel 2018, retrieved on Mar. 28, 2019, retrieved from the Internet at http://trialgardens.raker.com/trial-data/trial-detail/2018/4443, one page. (Year: 2018).*

* cited by examiner

*Primary Examiner* — June Hwu
(74) *Attorney, Agent, or Firm* — Koenig IP Works, PLLC

(57) ABSTRACT

'UF16-23-2' is a basil plant with vigorous upright growth habit, dark green leaf color, good lateral branching, late flowering and excellent resistance to Basil Downy Mildew (*Peronospora belbahrii*, BDM). It has a strong upright growth habit with excellent lateral branching which allows it to produce good quantities of high quality leaf tissue. Late flowering and BDM resistance in the greenhouse and field make this cultivar suitable for growers of fresh cut and potted basil for culinary use, and for home gardeners.

5 Drawing Sheets

ACKNOWLEDGMENT OF FEDERAL RESEARCH SUPPORT

This invention was made with government support under FLA-ENH-005355 awarded by the National Institute of Food and Agriculture, USDA. The government has certain rights in the invention.

Genus and species: *Ocimum* x *hybrida*.
Cultivar denomination: 'UF16-23-2'.

CROSS-REFERENCE TO RELATED APPLICATION n/a

BACKGROUND OF THE NEW CULTIVAR

The invention relates to a new and distinct cultivar of basil plant named 'UF16-23-2' that has been selected for good horticultural characteristics and resistance to basil downy mildew (BDM: *Peronospora belbahrii*). 'UF16-23-2' originated from interspecific crosses between BDM-susceptible *Ocimum basilicum* 'Caesar' and BDM-resistant *Ocimum americanum* (USDA accession PI 500945) made in Gainesville, Fla. in 2013-2014. All interspecific hybrids were BDM-resistant and self-sterile in the greenhouse. After being planted in an open-pollinated (OP) field with hundreds of other *Ocimum* hybrids in Citra, Fla. some of the interspecific hybrids ('UF14-9-3' and 'UF14-9-9') made a small number of seeds in Summer 2014. Several seedlings were selected from these OP interspecific hybrids, screened for BDM resistance, and used to produce advanced hybrids in Fall 2014. Two of these hybrid plants, 'UF14-127-13' and 'UF14-129-36', were crossed in a greenhouse in Gainesville, Fla. to produce a small number of hybrid seeds that were grown and selected in Spring 2015 for improved horticultural characteristics and BDM resistance. One selected hybrid resulting from this cross, 'UF15-13-5', was planted in a field with hundreds of other *Ocimum* hybrids in May-November 2015 in Citra, Fla. to produce OP seeds. The resulting seeds were grown and selected in Spring 2016 for improved horticultural characteristics and BDM resistance. In May 2016 one of these seedlings, 'UF16-23-2', was given elite status in our program and selected for further asexual propagation and trialing for garden performance and potential for culinary use.

'UF16-23-2' has been reproduced asexually for over 18 months through vegetative cuttings and has been found to retain its distinctive characteristics through successive asexual propagations. 'UF16-23-2' was first propagated asexually by meristem tip cuttings in May, 2016 in Gainesville, Fla., and has remained true-to-type since that time. 'UF16-23-2' has not been made publicly available more than one year prior to the filing date of this application.

When compared to the female parent 'UF15-13-5' (not patented), both plants are BDM resistant. 'UF16-23-2' has large leaves with serrated edges, while 'UF15-13-5' has smaller leaves that do not have a pronounced serration. 'UF16-23-2' has an extremely vigorous well-branched upright, erect habit and initiates flowering very late in the summer season, whereas 'UF15-13-5' is vigorous, but has less lateral branching and initiates flowers earlier.

'UF16-23-2' has similar dark green foliage color to the commercial sweet basil *Ocimum basilicum* 'Caeser' (commercial cultivar, not patented), and it has darker green leaves than the commercial sweet basil *Ocimum basilicum* 'Italian Large Leaf ' (commercial cultivar, not patented). The leaf shape of 'UF16-23-2' is very similar to that of 'Italian Large Leaf', but leaf size of 'UF16-23-2' is slightly smaller. Plant habit of 'UF16-23-2' is more similar to 'Italian Large Leaf' than 'Caesar', but it has more lateral branches and initiates flowers later than both cultivars.

SUMMARY OF THE INVENTION

The following are the most outstanding and distinguishing characteristics of 'UF16-23-2' when grown under normal horticultural practices in Gainesville, Fla. and Citra, Fla. 'UF16-23-2' has a combination of vigorous upright growth habit, dark green leaf color, good lateral branching, late flowering and excellent BDM resistance, which makes it significantly different than other commercial basil plants. It has a strong upright growth habit with excellent lateral branching when grown as a stock plant in the greenhouse, thus providing ample vegetative propagules for producers. Late flowering and BDM resistance in the greenhouse and field make this cultivar suitable for growers of fresh cut and potted basil for culinary use, and for home gardeners.

DESCRIPTION OF THE FIGURES

The accompanying figure and photographs (as shown in FIGS. 1-5) illustrate the overall appearance of the new basil cultivar 'UF16-23-2'. These photographs show the colors as true as can be reasonably obtained in colored reproductions of this type. Colors in the photographs may differ slightly from the color values cited in the detailed botanical description, which accurately describe the colors of the new basil cultivar.

DETAILED BOTANICAL DESCRIPTION OF THE CULTIVAR

Figure 1:
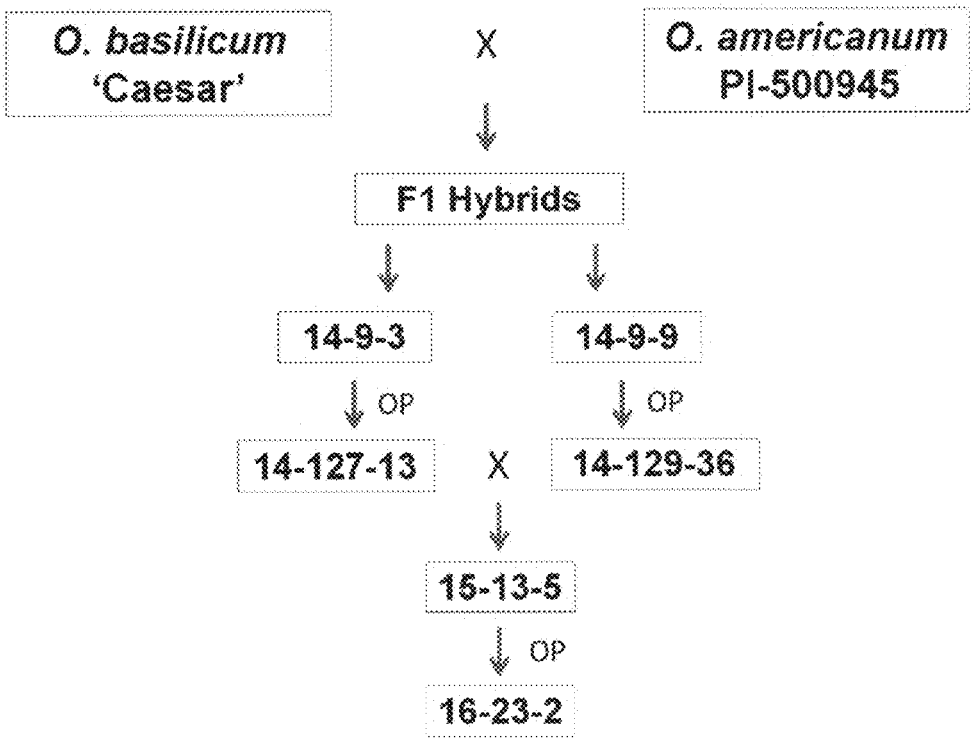
FIG. 1 shows the pedigree of the claimed plant ('UF16-23-2')
Figure 2:
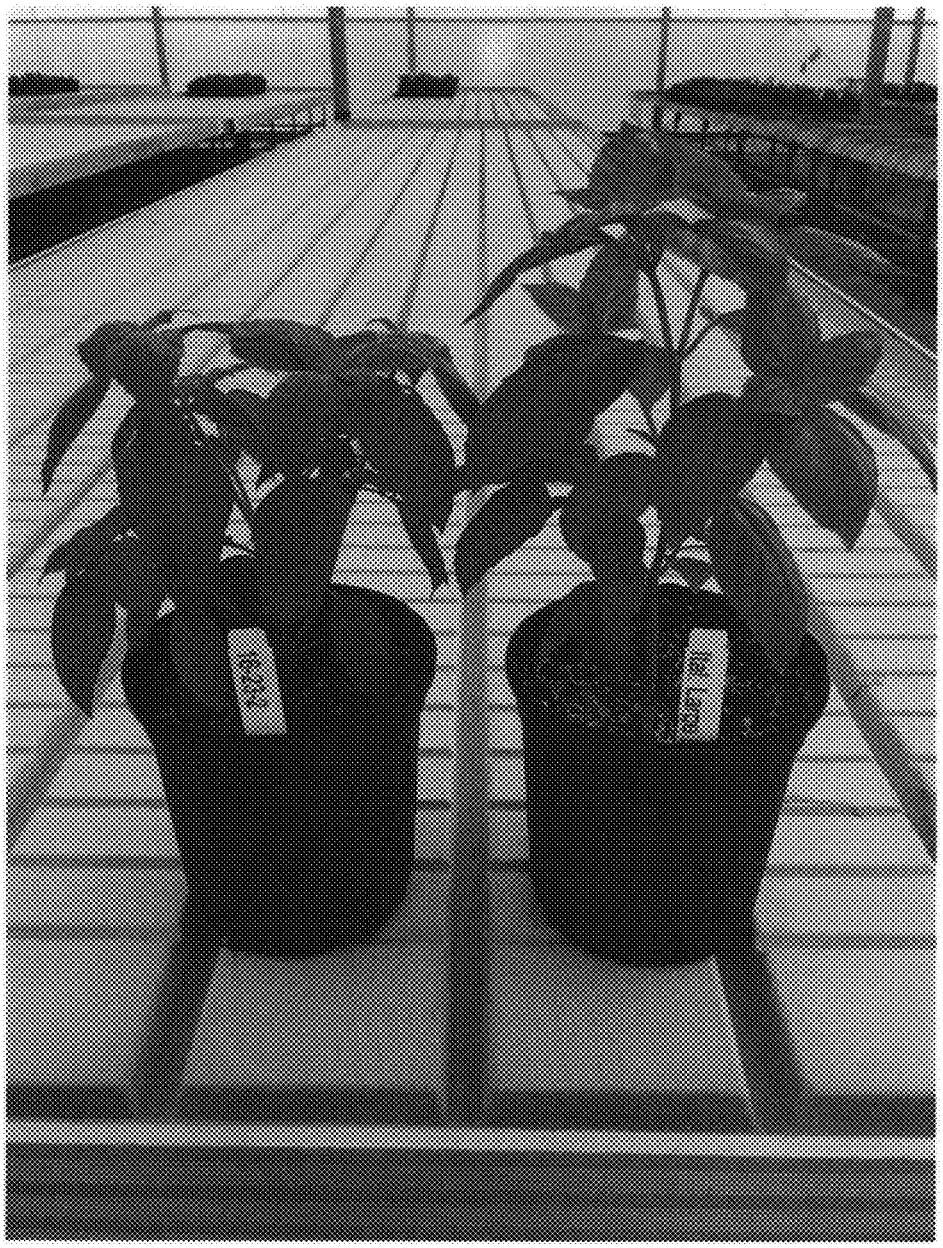
FIG. 2 shows the growth habit, form, and foliage of 'UF16-23-2' (left) compared to the commercial cultivar *Ocimum basilicum* 'Italian Large Leaf ' (right). Plants were grown from unrooted cuttings for six weeks in a warm greenhouse in late Summer 2017.
Figure 3:
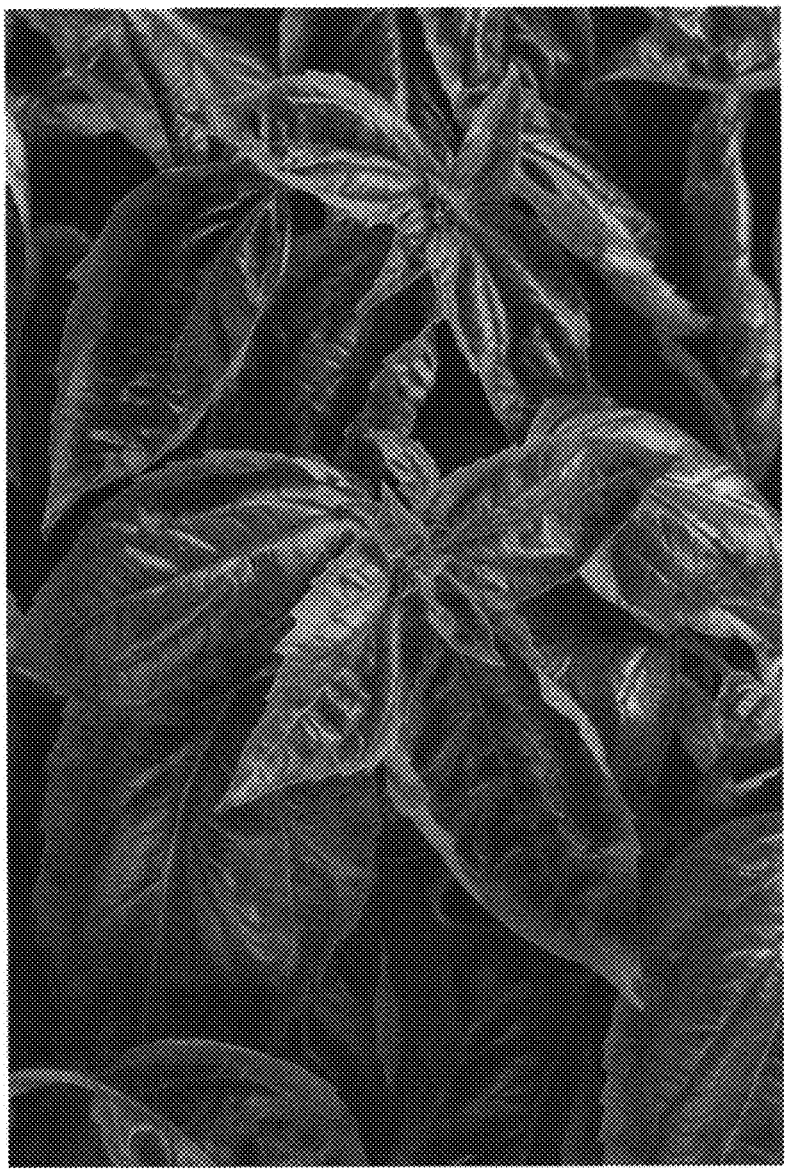
FIG. 3 shows a close-up view of the foliage of 'UF16-23-2'.
Figure 4:
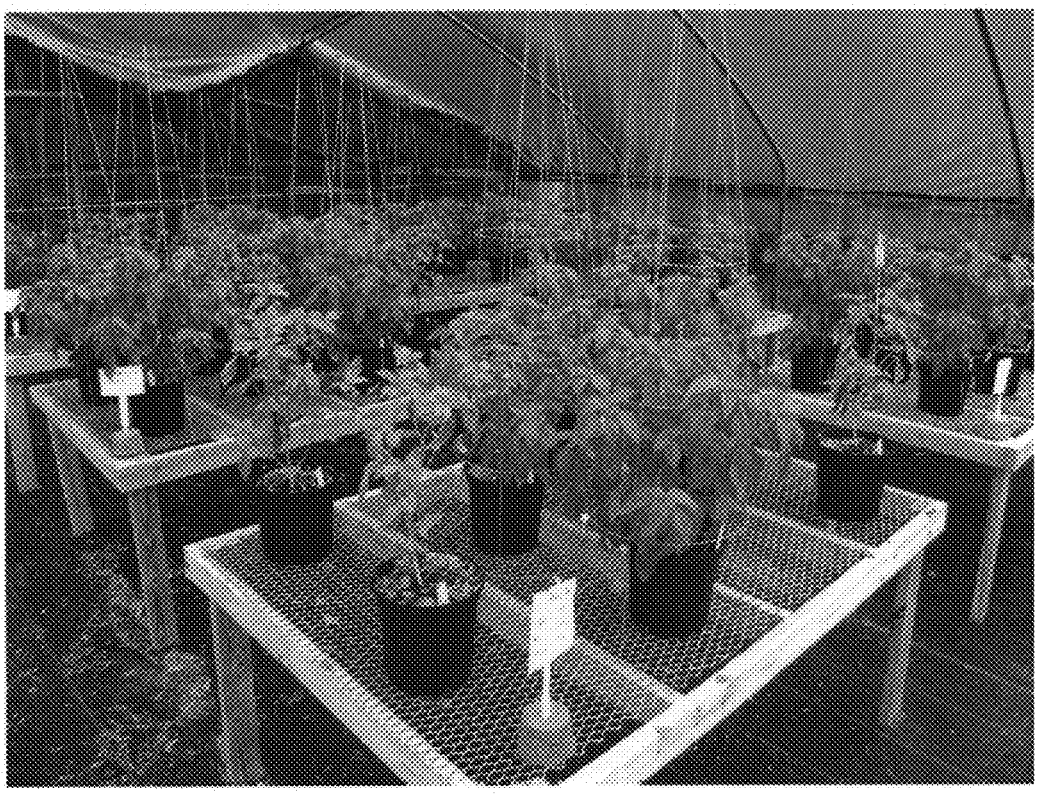
FIG. 4 shows the level of resistance to Basil Downy Mildew (*Peronospora belbahrii*, BDM) of 'UF16-23-2' compared to *Ocimum basilicum* 'Italian Large Leaf' in a small multi-plant trial. Plants were grown to full size in a warm greenhouse in late Summer 2017, and placed outdoors with no BDM inoculation and without fungicide sprays in late September 2017. Photos were taken one month after removal from the greenhouse.
Figure 5:
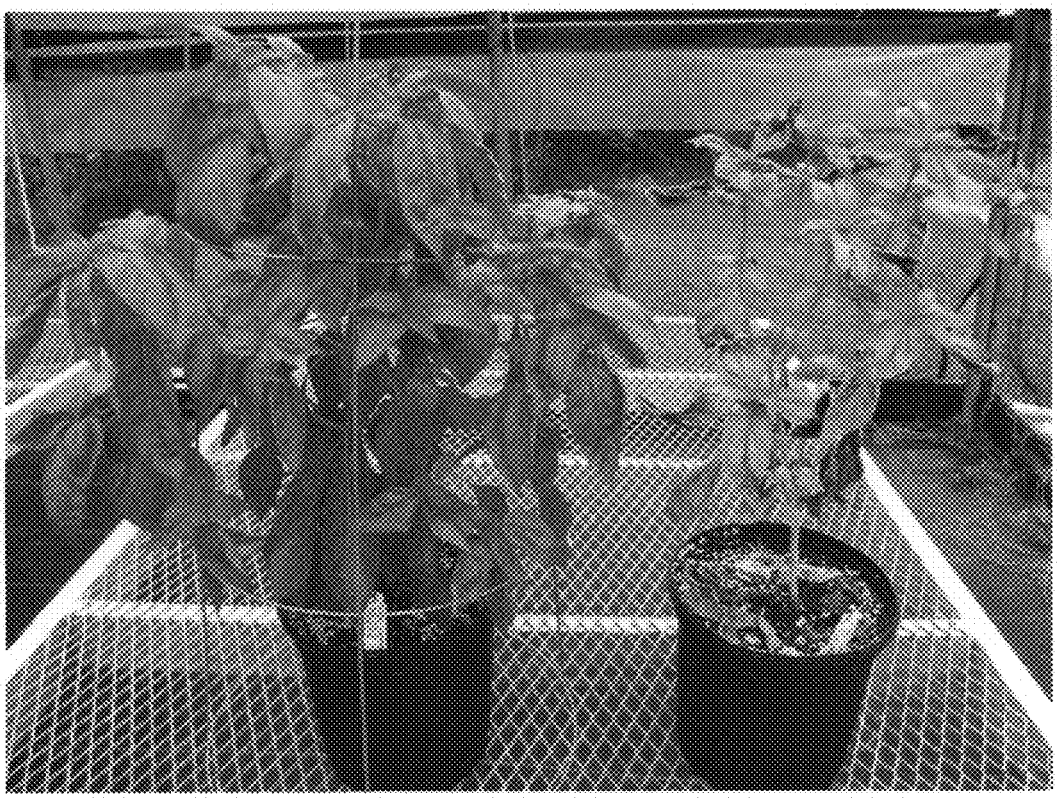
FIG. 5 shows a close-up view of the level of resistance to Basil Downy Mildew (*Peronospora belbahrii*) of 'UF16-23-2' (left) compared to *Ocimum basilicum* 'Italian Large Leaf' (right). Plants were grown to full size in a warm greenhouse in late Summer 2017, and placed outdoors with no BDM inoculation and without fungicide sprays in late September 2017. Photos were taken one month after removal from the greenhouse.

The following detailed description sets forth the distinctive characteristics of 'UF16-23-2'. The detailed description was obtained using twelve-week-old plants grown from unrooted meristem cuttings in Fall, 2017 in a poly-covered plastic greenhouse in Gainesville, Fla. The plants were propagated in mist for ten days after cuttings were stuck, then grown in two gallon pots for approximately ten additional weeks. Color references are to The R.H.S. Colour Chart of The Royal Horticultural Society of London (R.H.S.), 2007 5th Edition.

BOTANICAL DESCRIPTION

Botanical classification:
- *Family*.—Lamiaceae.
- *Botanical name*.—*Ocimum* x *hybrida* (*O. basilicum* x *O. americanum*).
- *Common name*.—Basil.
- *Cultivar*.—'UF16-23-2'.

Plant description:
- *Form*.—Erect.
- *Habit*.—Upright.
- *Height* (*from top of soil*).—70-75 cm.
- *Width* (*horizontal plant diameter*).—60-65 cm.

Propagation:
- *Type*.—Vegetative meristems having at least one node.
- *Time to initiate roots*.—3-4 days.
- *Time to produce a rooted cutting*.—7-10 days.
- *Root habit*.—Fibrous.
- *Root description*.—Callus forms in 2-3 days, roots initiate in 3-4 days and become a highly branched cutting in 7-10 days.

Branches:
- *Quantity per plant*.—Approximately 12.
- *Branch color*.—RHS 147D.
- *Texture*.—Pubescent.
- *Stem description*.—Square-shaped stem, 1.5-2.0 cm in diameter at the soil line.
- *Branch diameter*.—0.4-0.5 cm at the base of a 55 cm long branch.
- *Branch length*.—50-55 cm.
- *Internode length*.—7.0-7.5 cm.
- *Anthocyanin*.—Not present.

Leaves:
- *Quantity of leaves per branch*.—14-16.
- *Arrangement*.—Opposite.
- *Fragrance*.—Highly fragrant.
- *Shape*.—Ovate.
- *Cross-sectional shape*.—Convex.
- *Length*.—11-12 cm
- *Width*.—6-7 cm.
- *Apex*.—Broadly acuminate.
- *Base*.—Attenuate.
- *Margin*.—Serrate. Serration: Slightly serrated.
- *Leaf puckering*.—Weak to medium on mature leaf.
- *Leaf texture* (*both surfaces*).—Smooth.
- *Leaf glossiness*.—Medium.
- *Pubescence color* (*both surfaces*).—Not present.

*Venation color*.—Upper surface: Center: RHS 145D. Lower surface: RHS 145C.

*Venation pattern*.—Upper surface: Palmate. Lower surface: Palmate.

*Color*.—Immature leaf: Upper surface: RHS 143B. Lower surface: RHS 144B.

*Color*.—Mature leaf: Upper surface: RHS 137B. Lower surface: RHS 138B.

*Petiole length*.—3-4 cm.

*Petiole diameter*.—0.2-0.3 cm.

*Petiole color*.—RHS 145C.

*Petiole texture*.—Smooth, no pubescence.

Flower:

*Arrangement*.—Verticil.

*Aspect*.—None.

*Flowering habit* (*length of flowering season*).—Year-round, at least in USDA Hardiness Zones 8b-10b, hardy down to 0° C.

*Number of inflorescences per plant*.—Approximately 9.

*Number of flowers per inflorescence*.—Approximately 100 to 200, depending on length and developmental age of the inflorescence.

*Fragrance* (*if present, is it strong, medium, mild, spicy, sweet, etc.*).—None.

*Lastingness of individual bloom*.—3-5 days.

*Rate of opening*.—Approximately one whorl per day.

*Flower bud*.—Shape: Round. Length: Approximately 3.0 mm. Diameter: Approximately 2.2 mm. Color: RHS 157A. Texture: Hirsute.

*Corolla*.—Arrangement: Bilabiate. Length: Approximately 1.1 cm. Diameter: Approximately 0.7 cm. Upper lip: Length: Approximately 0.6 cm. Width: Approximately 0.7 cm Apex: Broad. Base: Narrow. Margin: Lobed. Texture (both surfaces): Smooth. Color: Upper surface: RHS NN155C. Lower surface: RHS NN155C. Lower lip: Length: Approximately 5.1 mm. Width: 3.1 mm. Apex: Broad with teeth. Base: Narrow. Margin: Lobed. Texture: Smooth. Color: Upper surface: RHS NN155C. Lower surface: RHS NN155C.

*Calyx*.—Number of sepals per flower: Approximately 5: three upper sepals with teeth and two lower sepals that are fused. Length: Approximately 3 mm. Diameter: Approximately 2.5 mm. Apex: Mucronate. Base: Rounded. Texture (both surfaces): Smooth with hairs along margin. Pubescence (present or absent): Hairs along margin. Sepal color: Upper surface: RHS 144A. Lower surface: RHS 144A.

*Pedicels*.—Angle: Approximately 90 degrees. Length: Approximately 4.0 mm. Diameter: Approximately 0.5 mm. Texture: Smooth. Color: RHS 143C.

*Peduncle*.—Length: 20 cm to 50 cm. Diameter: 0.2 cm to 0.4 cm. Texture: Pubescent. Color: RHS 143C.

Reproductive organs:

*Stamens*.—Number: Approximately 4. Filament: Approximately 4. Color: RHS NN155C. Length: Approximately 6.0 mm. Diameter: Approximately 0.19 mm. Anther color: RHS NN155C. Pollen amount: Moderate. Pollen color: RHS 11B.

*Pistils*.—Number per flower: Approximately 1. Pistil length: Approximately 8.0 mm. Stigma: Color: RHS 144A. Shape: Y-shaped. Length: Approximately 2.7 mm. Diameter: Approximately 0.3 mm. Style: Color: RHS NN155C. Length: Approximately 1.0 cm. Diameter: Approximately 0.18 mm. Ovary: Shape: Round. Color: RHS NN155C. Nutlets: Number: Four aborted embryos, each embryo being less than 0.1 cm in diameter.

Seeds:

*Seed shape*.—Round.

*Seed size*.—1.1 mm.

*Seed color*.—RHS 202A.

*Seed texture*.—Smooth.

Disease and insect resistance: Insect resistance is typical of the species, thus no claims are made of any superior insect resistance with this cultivar. The most common insect pests observed on this plant in Gainesville, Fla. have been greenhouse whiteflies (*Trialeurodes vaporariorum*), spider mites (*Tetranychus urticae*), and Western flower thrips (*Frankliniella occidentalis*), which occur on older stock plant material held in the greenhouse for over 3-4 months. The most common pathogen of this species in the U.S. is basil downy mildew (*Peronospora belbahrii*), and this plant is resistant to that pathogen.

We claim:

1. A new and distinct basil plant named 'UF16-23-2' as illustrated and described herein.

* * * * *